(12) United States Patent
Berdut-Teruel (10) Patent No.: US 11,229,807 B1
(45) Date of Patent: *Jan. 25, 2022

(54) MAGNETIC THERAPEUTIC DEVICE AND METHODS OF USING THE SAME

(71) Applicant: Elberto Berdut-Teruel, San Juan, PR (US)

(72) Inventor: Elberto Berdut-Teruel, San Juan, PR (US)

(*) Notice: Subject to any disclaimer, the term of this patent is extended or adjusted under 35 U.S.C. 154(b) by 0 days.

This patent is subject to a terminal disclaimer.

(21) Appl. No.: 17/011,614

(22) Filed: Sep. 3, 2020

Related U.S. Application Data (60) Provisional application No. 63/021,284, filed on May 7, 2020.

(51) Int. Cl.
*A61N 2/12* (2006.01)
*A61N 2/00* (2006.01)
*A61N 2/06* (2006.01)

(52) U.S. Cl.
CPC .......... *A61N 2/004* (2013.01); *A61N 2/06* (2013.01); *A61N 2/12* (2013.01)

(58) Field of Classification Search
CPC ... A61N 2/00; A61N 2/02; A61N 2/06; A61N 2/12; A61N 2/004
USPC .................................................. 600/9, 13–15
See application file for complete search history.

(56) References Cited

U.S. PATENT DOCUMENTS

| | | | |
|---|---|---|---|
| 5,642,739 A * | 7/1997 | Fareed ................... | A61F 5/0118 128/878 |
| 5,667,469 A * | 9/1997 | Zhang ...................... | A61N 2/12 600/9 |
| 5,782,743 A * | 7/1998 | Russell .................... | A61N 2/06 600/15 |
| 10,238,887 B1 * | 3/2019 | Berdut-Teruel ........ | A61N 2/004 |
| 2003/0009077 A1 * | 1/2003 | Woo ........................ | A61N 2/06 600/15 |
| 2015/0283396 A1 * | 10/2015 | Berdut-Teruel ........ | A61N 2/008 600/9 |

* cited by examiner

*Primary Examiner* — Samuel G Gilbert
(74) *Attorney, Agent, or Firm* — Luis Figarella (57) ABSTRACT

An improved apparatus and technique for realizing the benefits of magnetic therapy in the medical field, in which permanent magnet devices and optional accoutrements are positioned against various human body parts and portions. Preferably, the magnetic apparatus is relatively thin, and formed of ferrous and/or non-ferrous materials. The therapeutic effects of the magnetic apparatus are maximized, and the pad is maintained in contact with the body part through a specific treatment regime, providing a simple and economical way of realizing the benefits of magnetic therapy.

6 Claims, 12 Drawing Sheets

Figure 1

Prior Art

MAGNETIC THERAPEUTIC DEVICE AND METHODS OF USING THE SAME

CROSS-REFERENCE TO RELATED APPLICATIONS

This application is a continuation-in-part of U.S. Pat. Appl. 63/021,284 titled "Magnetic Therapeutic Device and Methods of Using the Same", filed on May 7, 2020 the disclosure of which is herein incorporated by reference in its entirety.

PATENTS CITED

The following documents and references are incorporated by reference in their entirety, Nakayama U.S. Pat. No. 3,291,620, Souder U.S. Patent Pub. No. 2013/0133872, Yang U.S. Pat. No. 5,891,331, Shimiyashu U.S. Pat. No. 4,480,596; Smith et al U.S. Pat. No. 6,623,419, Martello U.S. Pat. No. 6,551,234, Getek, U.S. Pat. No. 6,406,418, Roberts et al U.S. Pat. No. 6,632,168, Steponovich, U.S. Pat. No. 6,610,023, Juster et al, U.S. Pat. No. 6,344,021, Engel U.S. Pat. No. 6,146,324, Nagler U.S. Pat. No. 6,093,143, Snider U.S. Pat. No. 5,336,498, Russell U.S. Pat. No. 5,782,743, Griffin et al U.S. Pat. No. 4,587,956, Chiu U.S. Pat. No. 5,989,178, Ishikawa U.S. Pat. No. 4,095,587, Monden et a U.S. Pat. No. 4,186,567, Li et al U.S. Pat. No. 5,226,020, Haglund U.S. Pat. No. 6,053,859, Paturu U.S. Patent Pub. 20020151759, Ross U.S. Pat. No. 5,718,721, Fichell et al U.S. Pat. No. 6,402,678, Wascher et al U.S. Pat. No. 6,443,882, Nakamichi U.S. Pat. Pub. No. 20130207759, Ardizzone et al U.S. Pat. No. 6,383,129, Riach U.S. Pat. Pub. No. 20050139215 and Bouldin et al U.S. Pat. No. 6,149,577.

FIELD OF THE INVENTION

This invention relates to a magnetic therapeutic device and methods for its use for therapeutic purposes. More particularly, this invention relates to a magnetic device and a process to treat and or prevent conditions such as viral infections, body pain, sleeplessness, menstrual pain, depression and other stress related conditions or diseases comprising the said magnetic therapeutic device.

DESCRIPTION OF THE RELATED ART

The prior art discloses many inventions wherein a variety of devices or items containing magnets are described and recommended for treating, preventing or improving diverse health conditions.

Nichols, U.S. Pat. No. 6,147,277 discloses a device and method to provide equine therapeutics via an attachable device and instructions for its use. Yang, U.S. Pat. No. 5,891,331 discloses a portable magnetic device similar to a fountain pen and useful in purifying water and other drinks by exposing the said liquids to bio ceramics and magnets. The said magnetized liquids are said to promote blood circulation as well as to improve digestion and absorption.

Nakayama, U.S. Pat. No. 3,921,620, Shimiyashu, U.S. Pat. No. 4,480,596; Smith et al, U.S. Pat. No. 6,623,419 as well as Martello U.S. Pat. No. 6,551,234 are examples of US Patents wherein therapeutic magnetic belts are used in order to reduce musculoskeletal pain, counteract fat and or reducing muscles stiffness by exposing the described body areas to magnetic flux.

Steponovich, U.S. Pat. No. 6,610,023 discloses a strap having magnets that is conveniently wrapped around the knee, giving support to the knee joint that allows the wearer to have maximum knee activity while helping him or her to overcome pain and diseases associated with the knee.

Furthermore, magnetic body ornaments and/or jewelry, such as rings, bracelets, necklaces, chain belts, earrings and wrist watches have been already disclosed in patented publications, such as Chiu U.S. Pat. No. 5,989,178, Ishikawa U.S. Pat. No. 4,095,587, Monden et al U.S. Pat. No. 4,186,567 and Li et al U.S. Pat. No. 5,226,020, among others. The said items are said to promote health conditions in the wearer and in many instances preventing the wearer of getting ill.

The prior art also discloses other multiple magnetic items such as shoes, pillows and gloves that are intended to promote health via exposing the body to the magnetic flux integrated in the said items, see for instance, Qui et al U.S. Pat. No. 6,151,807, Greenwalt U.S. Pat. No. 5,976,100, Komuro U.S. Pat. No. 5,193,236 and Chen U.S. Pat. No. 6,085,355, among others.

Interestingly, some magneto-therapeutic devices are designed to treat particular medical conditions, for instance, Riach U.S. Pat. Pub. No. 20050139215 as well as Haglund U.S. Pat. No. 6,053,859 disclose a magnetic apparatus and method comprising the same in the treatment of sinus conditions. Paturu U.S. Patent Application publication 20020151759 discloses a method for treatment of erectile dysfunction, peripheral vascular disease, cerebral insufficiency and certain vascular pathologies. Ross U.S. Pat. No. 5,718,721 and Fichell et al U.S. Pat. No. 6,402,678 disclose methods for the treating of migraine headache pain by exposing selective parts of the body to magnetic flux.

Wascher et al U.S. Pat. No. 6,443,882 and Bouldin et al U.S. Pat. No. 6,149,577 disclose an apparatus and method comprising the said magneto therapeutic device in the treatment of degenerative diseases and disorders. The full contents of the above cited references are herein incorporated by reference in their entirety.

In general terms, the prior art recognizes that the magneto therapy functions in the treatment of multiple medical diseases and/or conditions by increasing the blood circulation and energizing a particular part of the body once it is exposed to the magnetic energy or flux of magnets. Increasing blood's circulation helps to oxygenate the vital organs and tissues and help to clear up veins and arteries, stimulating the body to promote its healing function naturally.

There is a need for new apparatuses and methods for using magneto therapeutic devices in treating viral, bacterial, fungus and other infections. Placing magnets across the blood flow could help with viral inspections such as Corona, COVID19, HIV, Leukemia, Flu, Chickungunya, Palsy, Typhoid, tuberculosis, Smallpox, Measles, Chickenpox, Insomnia and other medical conditions that may also include diseases that include migraine, muscle pain, sleeplessness, menstrual pain, stress related conditions and/or diseases, wherein the said method is a noninvasive technique that does not requires the use of medical compositions and lacks any risks of pernicious secondary effects.

SUMMARY OF THE INVENTION

This section is for the purpose of summarizing some aspects of the present invention and to briefly introduce some preferred embodiments. Simplifications or omissions may be made to avoid obscuring the purpose of the section.

Such simplifications or omissions are not intended to limit the scope of the present invention.

In one aspect, the invention is about a magnetic blood cell virus therapy apparatus comprising: two or more permanent magnet mounting locations along a length of flexible or semi-flexible mechanical linkage component, at least one said mounting locations containing a North Polarity magnet, and at least one other having a South Polarity magnet, wherein said mechanical linkage component is adjustable so that it may hold two or more of said magnet locations against a human body part within the circumference formed by said mechanical linkage when closed. In another aspect said flexible or semi-flexible mechanical linkage is comprised of one or more of the following: a belt, strap, chain, flexible metal collar; and each said element is positioned around an individual's neck.

In one aspect the invention is about a method for magnetic blood cell virus therapy comprising the steps of: positioning at or near a human body portion's skin surface a magnetic apparatus, wherein said magnetic apparatus has two or more permanent magnet mounting locations along a length of flexible or semi-flexible mechanical linkage component, wherein at least one said mounting locations containing a North Polarity magnet, and at least one other having a South Polarity magnet, wherein said mechanical linkage component is adjustable so that it may hold two or more of said magnet locations against a human body part within the circumference formed by said mechanical linkage when closed and placing said magnetic apparatus along a portion of a human body. In another aspect said flexible or semi-flexible mechanical linkage is comprised of one or more of the following: a belt, strap, chain, flexible metal collar; and each said element is positioned around an individual's neck for at least an hour a day.

In one aspect the invention is about a method for magnetic magnet blood cell oxygenation therapy comprising the steps of: positioning at or near a human body portion's skin surface a magnetic apparatus, wherein said magnetic apparatus has a handle connected to a body comprised of two or more permanent magnet mounting locations separated by a spatial gap, wherein said main body is made of a durable material capable of keeping each said permanent magnet mounting location aligned to each other, wherein one or more first permanent magnet magnetic elements, each positioned on an individual first permanent magnet magnetic element mounting station with a magnetic polarity North to South, wherein each said first magnetic element is permanently mechanically mounted so that its South polarity side is fixed in place and parallel to said main body and one or more second permanent magnet magnetic elements, each positioned on an individual second permanent magnet magnetic element mounting station with a magnetic polarity South to North, wherein each said second magnetic element is permanently mechanically mounted so that its North polarity side is fixed in place and parallel to said main body, wherein at least one of said first permanent magnet magnetic element(s) and at least one of said second permanent magnetic element(s) come in contact with said human body portion's skin, placing said magnetic apparatus along a portion of a human body and displacing said magnetic apparatus in a linear fashion along parallel to said human body portion's surface.

In another aspect said magnetic apparatus linear fashion displacement is accomplished through manual means. In yet another aspect placing a metal plate having an area size equal or larger to that of the human body portion to be treated so that said human body part rests on said metal plate. In another aspect placing said magnetic apparatus along a portion of a human body; and displacing said magnetic apparatus in a linear fashion parallel to said human body portion's surface for a distance that overlaps the area of said metal plate. In yet another aspect placing another magnetic apparatus on the opposite side of the human body portion being treated, so that said body portion is sandwiched between said magnetic apparatuses. In another aspect placing another magnetic apparatus on the opposite side of the human body portion's surface being treated, so that said body portion is sandwiched between said magnetic apparatuses, wherein the magnets are facing each other across the body part in a complementary magnetic polarity configuration.

Other features and advantages of the present invention will become apparent upon examining the following detailed description of an embodiment thereof, taken in conjunction with the attached drawings.

The above-described and other features will be appreciated and understood by those skilled in the art from the following detailed description, drawings, and appended claims.

DETAILED DESCRIPTION OF THE INVENTION

To provide an overall understanding of the invention, certain illustrative embodiments and examples will now be described. However, it will be understood by one of ordinary skill in the art that the same or equivalent functions and sequences may be accomplished by different embodiments that are also intended to be encompassed within the spirit and scope of the disclosure. The compositions, apparatuses, systems and/or methods described herein may be adapted and modified as is appropriate for the application being addressed and that those described herein may be employed in other suitable applications, and that such other additions and modifications will not depart from the scope hereof.

Simplifications or omissions may be made to avoid obscuring the purpose of the section. Such simplifications or omissions are not intended to limit the scope of the present invention. All references, including any patents or patent applications cited in this specification are hereby incorporated by reference. No admission is made that any reference constitutes prior art. The discussion of the references states what their authors assert, and the applicants reserve the right to challenge the accuracy and pertinence of the cited documents. It will be clearly understood that, although a number of prior art publications are referred to herein, this reference does not constitute an admission that any of these documents form part of the common general knowledge in the art.

As used in the specification and claims, the singular forms "a", "an" and "the" include plural references unless the context clearly dictates otherwise. For example, the term "a transaction" may include a plurality of transaction unless the context clearly dictates otherwise. As used in the specification and claims, singular names or types referenced include variations within the family of said name unless the context clearly dictates otherwise.

Certain terminology is used in the following description for convenience only and is not limiting. The words "lower," "upper," "bottom," "top," "front," "back," "left," "right" and "sides" designate directions in the drawings to which reference is made, but are not limiting with respect to the orientation in which the modules or any assembly of them may be used.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning—i.e. that it will be taken to mean an inclusion of not only the listed components it directly references, but also other non-specified components or elements. This rationale will also be used when the term 'comprised' or 'comprising' is used in relation to one or more steps in a method or process.

The present invention relates to the use of permanent magnets and their magnetic fields in the treatment of living tissue. Ron Laurence describes in his book "Magnet Therapy, The Pain Cure Alternative", Prima Lifestyles, ISBN 978-0761515470 (the content of which is herein incorporated by reference in its entirety), that among other areas, the effect of magnetic fields in the blood cells containing hemoglobin is significant given their high iron content.

Figure 1:
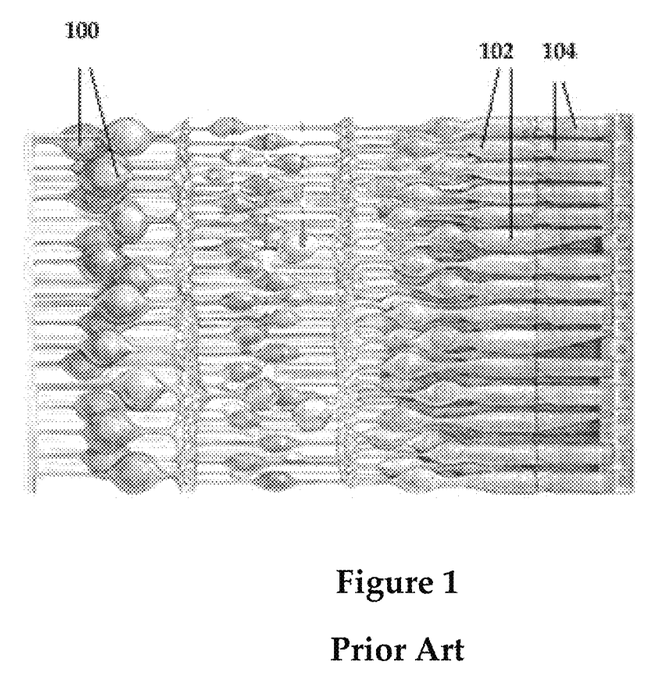
FIG. 1 shows an illustration of an eye optical nerve, as prior art.

Bipolar cells, such as FIG. 1 retinal ganglion cells 100 found in the eye, have the signals transmitted from the eye cones 102 and rods 104 through direct and indirect channels. Each type of bipolar cell establishes excitement connections with a corresponding ganglion cell 100. The visual information is passed through the eye cones 102 through one of two existing channels in the retina. Central cones within the reception field (RF) of the ganglion cells establish direct synaptic connections with the bipolar cells, known as direct of vertical connections. The signals coming from the peripheral cones of the RF taken an indirect route, going through the horizontal or lateral path (where the amacrine cells establish a feedback path towards the central cones of the bipolar cell RF).

All the retinal cells transmit their visual signals through the electronic effect, that is, through an electric current flux in the cytoplasm from the point of excitation through the presynaptic terminal (passive signal transmission). This allows for a gradual conductivity of the signal intensity. In this way, the intensity of the signal representing the hyper-polarization of the cones and rods within the retina is representative of the gradual illumination intensity (as opposed to a binary all or nothing signal). Since the axons of the ganglion cells (constituting the optical nerve) have to travel significant distances to the brain, the signals are best transferred as differential signals.

When the cones from the center of the RF are activated, the bipolar cells connected to the center are depolarized, while the bipolar cells disconnected from the center are hyper-polarized. The activation of the peripheral cones has the opposite response. There are two types of bipolar cells, de-polarizing and hyper-polarizing. When the cones and rods are excited, some bipolar cells de-polarized and the other hyper-polarized. This allows half of the cells to transmit positive signals and the other half to transmit negative signals.

A bipolar cell is a type of neuron which has two extensions. Bipolar cells are specialized within sensory neurons, those used for the transmitting of sensorial organs. As such, they are part of the smell, visual, taste, hearing and other vestibular functions. The most common cases include bipolar cells in the retina, vestibular nerves and the extensive use of bipolar cells to transmit body signals for the control of muscles.

Bipolar cells are also found in the spinal lymph nodes when the cells are in an embryonic stage. Sometimes, these extensions called processes, which exit the opposite poles of the cells, and the cell is assumed to have a 'bone' shape. In other cells, these extensions exit from the same point.

Magnetic therapies (whether through manual or machine assisted motion) accelerate the movement of the blood cells, affecting particularly hemoglobin cells, due to their large iron content. The device movements may be circular, semi-circular, linear or any other suitable combination. By using this method over any body part (not just blood vessel locations), such as locations with lacerations, open wounds, tumors, cancerous spots, inflamed spots, injured spots, cuts, grazes and other lesions. These magnetic therapies oxygenate the blood, preventing aging and general deterioration.

In cases where both fibers are apparently connected to a cell, one of the fibers is really a derivation from an adjacent nervous cell and ends in a ramification around the ganglion cell, or again, may be wrapped as a spiral around the nerve process emitted from the cell.

Figure 2:
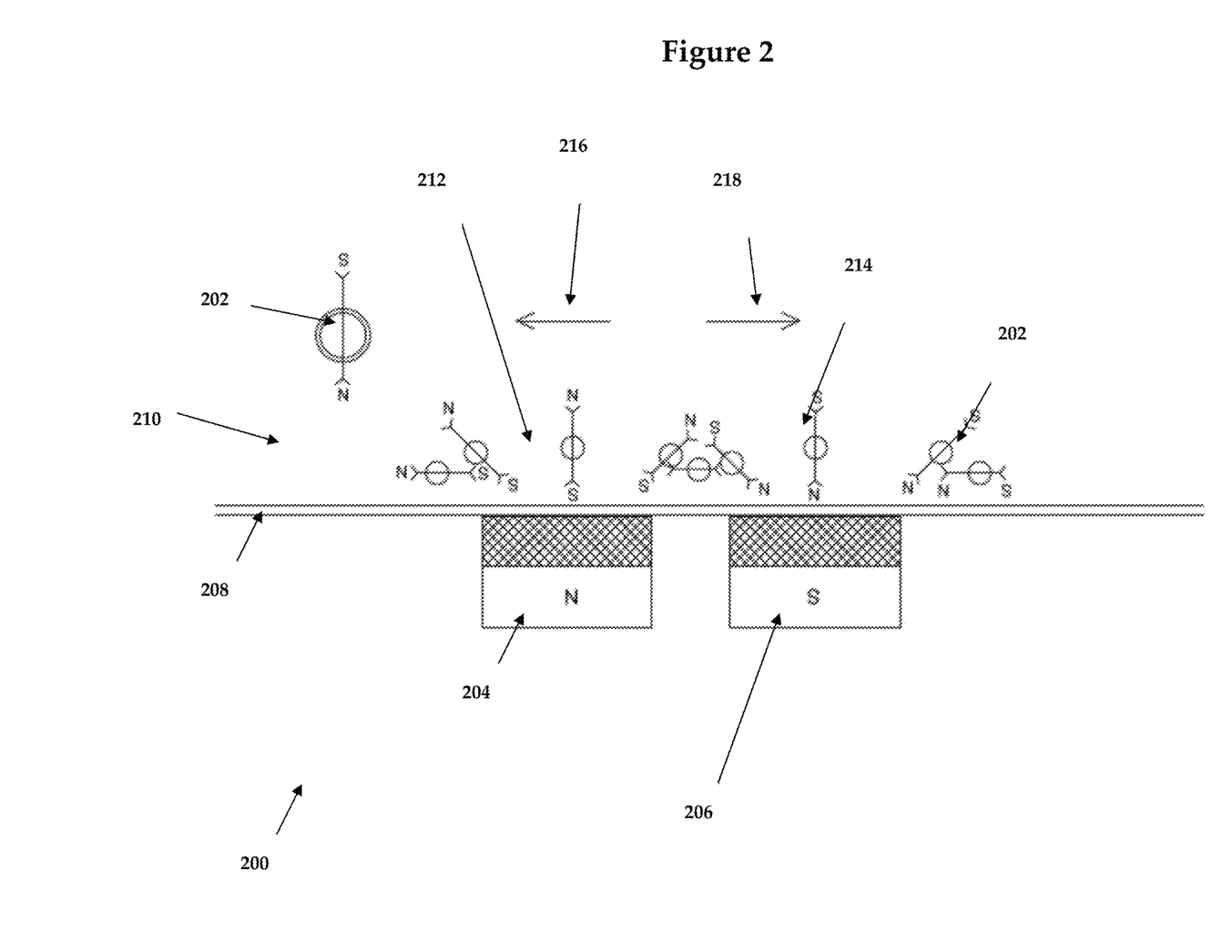
FIG. 2 illustrates the effect of one or more magnets on blood cells, according to an exemplary embodiment of the invention.

Referring to FIG. 2, we see 200 the effect of a permanent magnet's polarity (North Polarity or N-Pol 204 and the South Polarity or S-Pol 206) in the alignment of the North/South magnetic poles exhibited by blood cells 202 travelling in either direction 216 or 218 (or due to the movement of the magnet's polarity 204/206) within the blood vessel 210.

Note that while we describe the system in an embodiment using permanent magnets (such as those that are obtained by processing rare earth elements), the proposed solutions could be implemented using electromagnets and other artificial magnetic field generation methods and implements.

So if we locate (either in a fixed or moving condition) a magnet with an N-Pol 204 magnet anywhere near/at our skin 208 where it is near a blood vessel 210, the blood cells 202 travelling in said vessel in the 218 direction will align their magnetic axis to that of the N-Pol magnet 212 to begin with (Similarly, cells traveling in the 216 direction will enter the S-Pol magnetic field 206 first). Blood cells entering the magnetic field will have the hemoglobin and other 'metallic' components within them induce a polarity on the cell 202, causing it to spin 212 in response to the magnet's fields 204/206 via the natural inducement of magnetic polarity and the subsequent attraction to one 204 or the other 206 magnet's field polarity.

Figure 4:
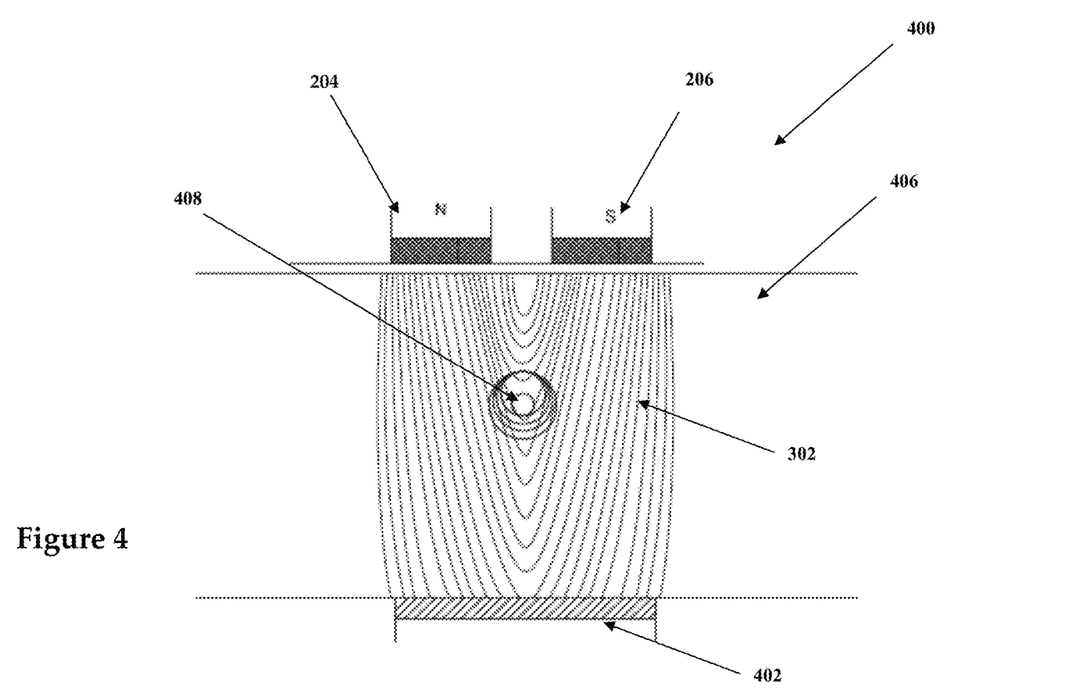
FIG. 4 illustrates the effect of one or more magnets on blood cells when a back-metal plate is used, according to an exemplary embodiment of the invention.
Figure 5:
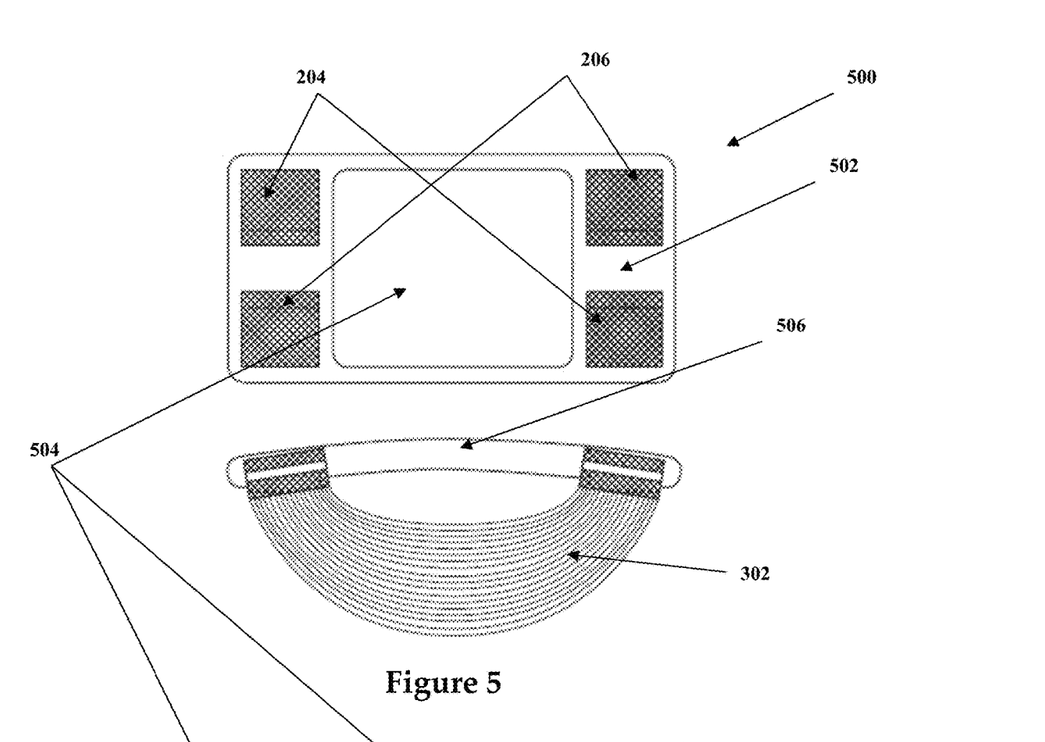
FIGS. 5-9 illustrate various product configurations, according to exemplary embodiments of the invention.
Figure 6:
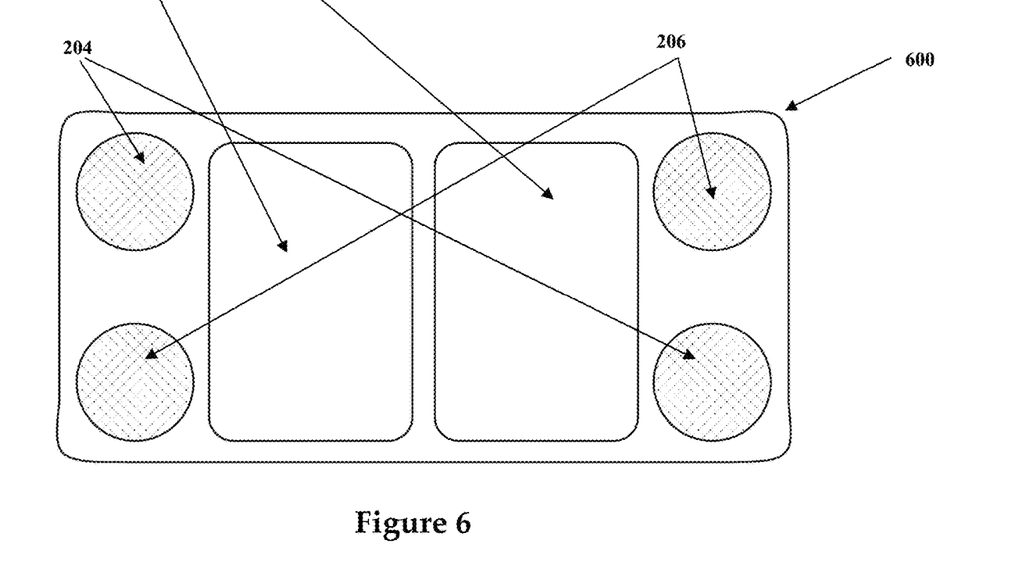
Figure 7:
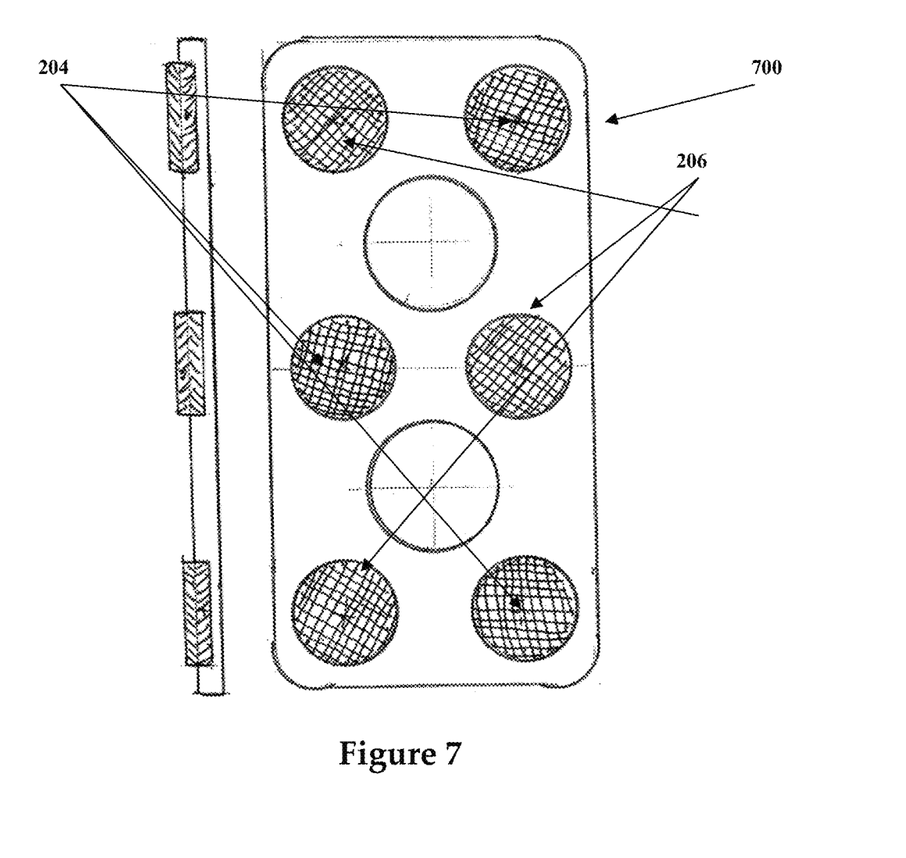

The enhanced rotation of the cells (induced by the cells magnetic pole rotation first at 212 later at 214 as the rotated cell encounters the S-Pol field of the magnet) forces said cell 202 to align 214 with the S-Pol magnet 206. Of course, the external movement of the magnets 204/206 would increase these effects, but even if the magnets are fixed, the blood flow will accomplish the effects. Similarly, the presence of an optional ferrous metal component 402 on the other side of the magnet (across the blood flow vessel 210, say on the other side of the body) sandwiching the blood vessel between it and the magnet, could have magnetic field augmentation possibilities.

Note that the permanent magnets 204, 206 comprising the magnetic elements described may contain variable magnetic strength and shapes. The term magnetic element herein used is intended to describe the part of the device containing one or more magnets. If more than one magnet is used in a given magnetic element, they may be placed in a stacked configuration. The phrase stacked configurations are intended to mean herein that a magnet is magnetically placed over the top of the other successively, thus each stack of magnets forming what is herein called a magnetic element unit.

Optionally, magnets may also be glued to one another even when they are magnetically attractive to each other. In case of the embodiment wherein the plate is used, a magnet may be placed at the bottom surface of the said plate while one or more can be placed on the top surface. Whenever the said plate is not magnetically attractive to the magnets placed over it, they may be glued to the said surface.

The magnets herein disclosed may be formed from any suitable magnetic material, preferably from rare earth, neodymium, ceramic or mixture thereof. The intensity of the magnetic force of the magnets may be varied and easily increased or decreased by the user by simply adding or subtracting magnets from the device at the wearer's convenience.

This alignment (212, 214) of the blood cells 202 has a number of beneficial effects. The primary one, is that it oxygenates the cells 202, provoking a neutralizing of the Ph of the cells, which liberates oxygen at the cell, energizing the cell's enzymes and as a result augmenting the Adenosine triphosphate (ATP) balance within the cell, which results in energy liberation. Cells renew their energy, making all cells (particularly weak ones) more resistant to virus, bacteria and disease.

The process also drains the metabolic toxins within the cell, such as Lactic Acid and diminishes the cellular swelling caused by effects such as Cytotoxic Edema. The affected skin area, as an example the pituitary gland, may become more active in the production of melatonin, a process that is associated with restorative sleep. While early in the work, there are significant effects vis-á-vis viruses like COVID-19. The human body is a marvel of self-restoration, sometimes inhibited by our own actions. Some of these include our eating habits, living habits, living enclosures and conditions, etc. Magnetic therapy allows our organisms to renew themselves. By enhancing how we produce chemicals and mineral, the body has improved performance against migraines and other such illnesses.

Figure 3:
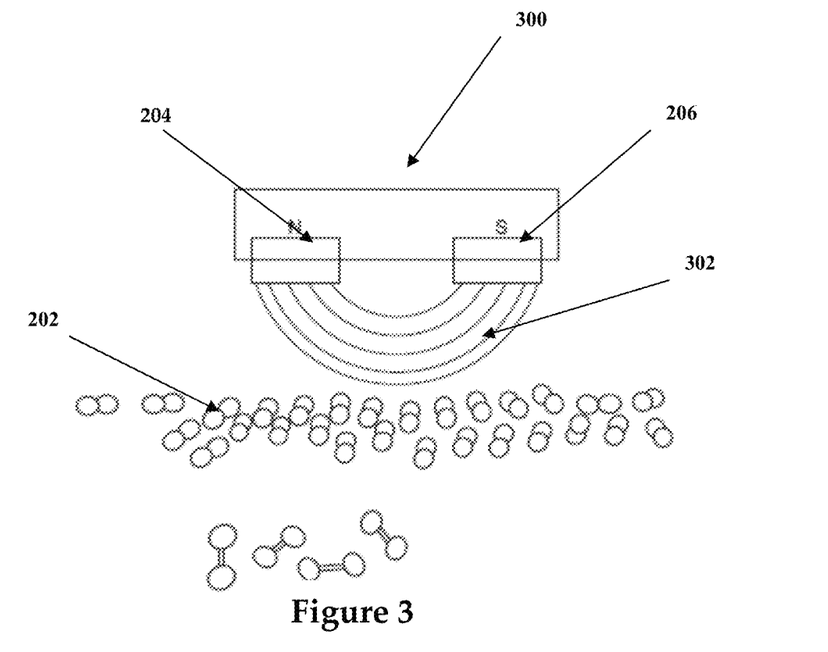
FIG. 3 illustrates the effect of one or more magnets on blood cells, according to an exemplary embodiment of the invention.

Referring to FIG. 3, we see 300 the effect of dual polarity magnets 204, 206 and the magnetic flux field between 302 would have on the blood cells 202, an effect that would be magnified by the movement of the magnets 204, 204 back and forth. In FIG. 4 we see 400 how the magnetic flux field 302 is augmented for particularly deep body portions by the placement of a ferrous (or optionally a non-ferrous) metal plate 402 across the body part 406, placing a tumor or other growth 408 across the magnetic flux field 302.

Figures 13, 14:
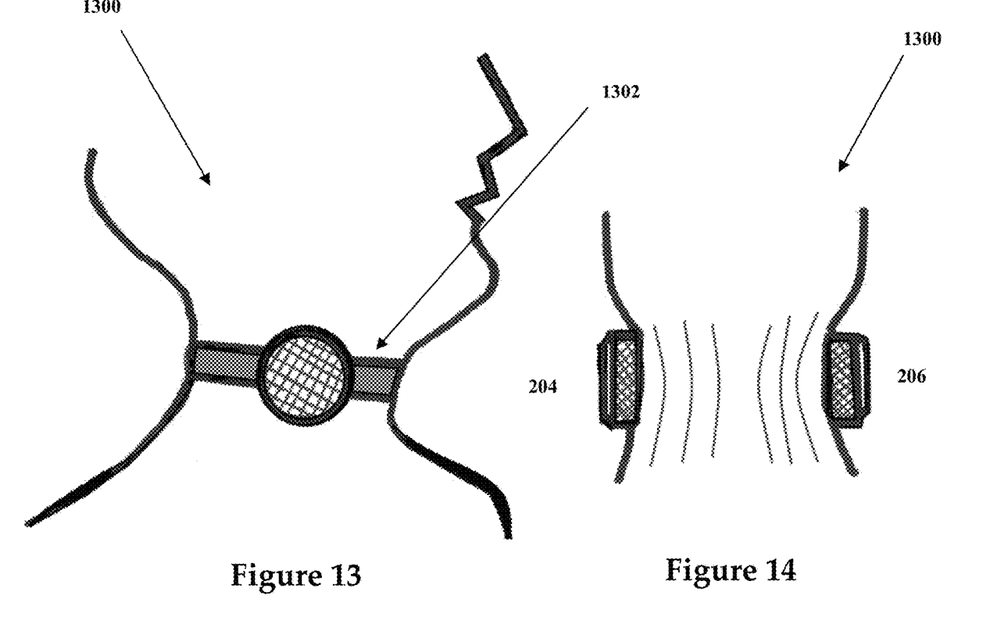
FIGS. 13-14 illustrate product configurations for viral, bacterial, fungus and other infections, according to exemplary embodiments of the invention, according to exemplary embodiments of the invention.
Figure 15:
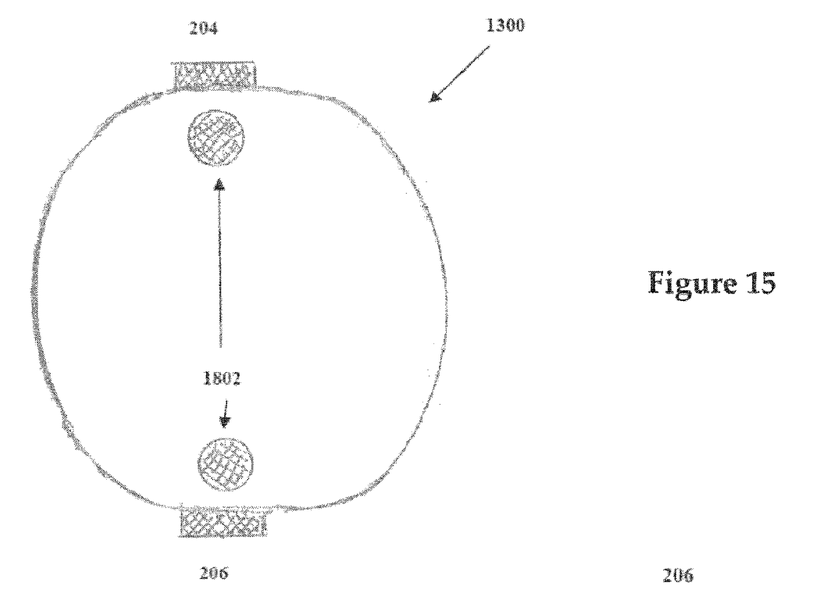
FIGS. 15-16 illustrate top views of product configurations for viral, bacterial, fungus and other infections, according to exemplary embodiments of the invention.
Figure 16:
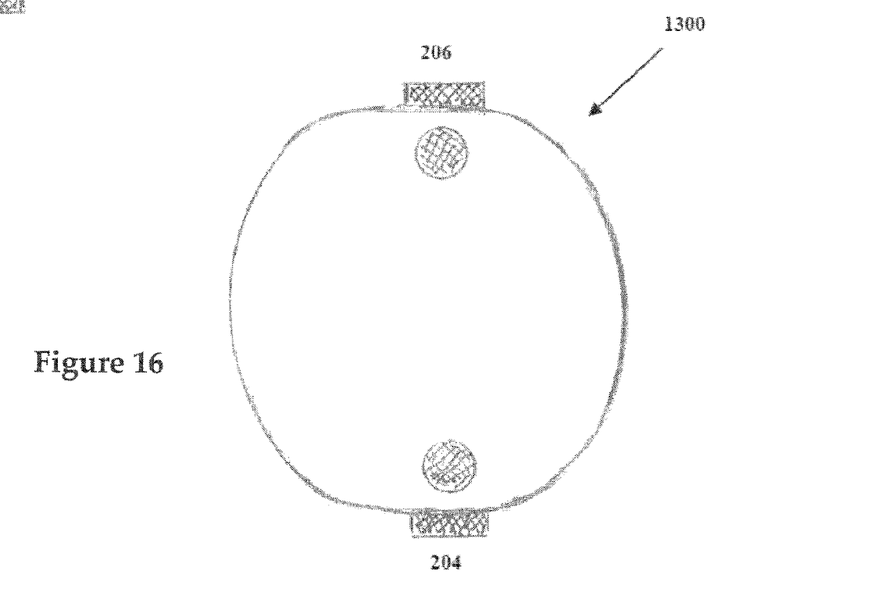

Referring to FIGS. 5-9, we see 500 a multi magnet 204, 206 arrangements having a large format and an optional curve 506 or flexible material so that it may fit the body curvature of a patient requiring large area treatment and an open portion 504. In one embodiment, the main body 502 forms a primary plane along which the permanent magnet mounting stations (one or more for the north polarity magnet and one or more for the south polarity magnet installation areas) are recessed openings in it. This allows for the magnets to be installed by one or a combination of chemical means (i.e. glue), mechanical means (i.e. pressure fittings, screw, rim rings), or even magnetic means (by making the back of the body 502 metallic, and having the magnets attach to the recess back surface. We see that the magnetic flux field 302 may cover a large area. Note the magnets may be alternated from the 204-206:206-204 shown to a 204-204:206-206 (FIGS. 12, 14-16) other suitable arrangements. Similar arrangements can be seen in FIGS. 7 and 13.

In one embedment (FIGS. 5 and 9), the curve 506 is also critical when placing the unit against a metal base plate 902 either for storage or against thin body parts, where there is a risk that the magnets may act as a 'bear trap' and snap the user. Or get so attached to each other that they become hard to separate. A similar problem occurs when two units are placed against each other (with the N-S polarity magnets matched), in that the same tight attachment may happen. The natural curve 506 or other shape would assist prevent such stiction.

Figure 8:
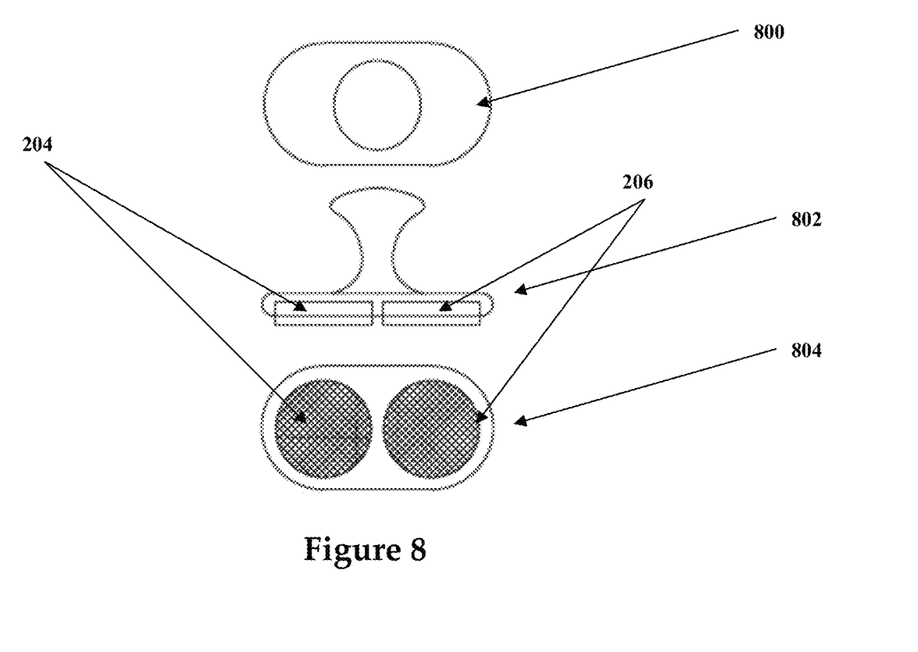

Referring to FIG. 8, we see a two magnet device (top view 800, side view 802 and bottom view 804) where two magnets 204/206 allow the user to place the unit over the skin and move it either in circular, linear or any combination of movements, allowing the magnetic field to induce its effects on the cells 202.

In a similar fashion, the magnets may be attached to semi-flexible 'body armor type' panels shaped like the body contour. Such an attachment would allow for the units to be fixed at/near the body site of interest, and then wrapped with a belt or girdle surrounding the body.

Figure 9:
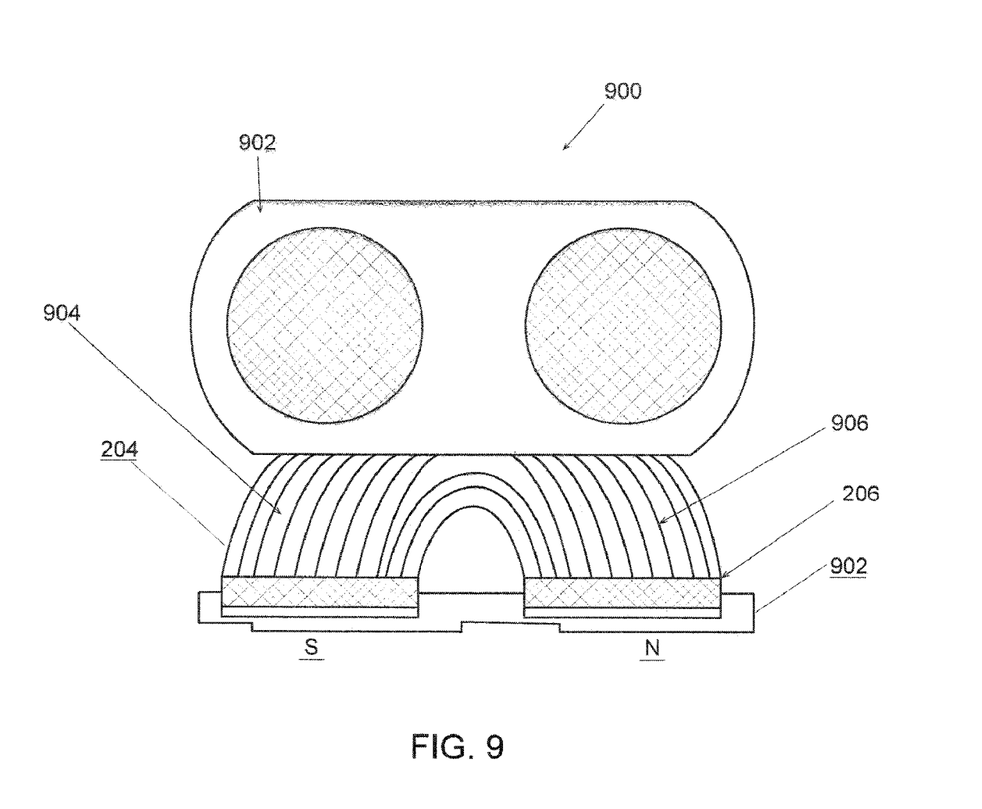

We see that in one embodiment 900 the device is optimized for the treatment of hemorrhoids, prostate, lacerations, ulcers, spine, hips and/or any situation where an arcuate or surrounding therapy may be limited. A pair of magnet elements 204/206 of North/South polarity are placed next to each other on a base plate 902. The magnetic flux 904/906 between said magnetic elements 204/206 offers the user the advantage of having one or more portions of their body subjected to the benefits of the magnetic flux, without having to surround it. In an alternate embodiment, another similar magnetic unit (either with a complementary magnetic polarity (i.e. N-S or S-N) or with the same polarity (N-N or S-S) is placed on the other side of the body (across the arm, the torso, the head) in order to magnify the effect of the flux crossing the body.

The main body base plate 902 on which the magnets (204, 206) are mounted may be constructed of any suitable material, including ferrous and non-ferrous metals, as well as thermoplastics or any other suitable material that is strong enough to hold both materials. A matching and optional metal plate 402 made of a ferrous material may be provided to increase the magnetic flux 904/906 when appropriate. The cavity may be left open or filled with a suitable material (ferrous metal, non-ferrous metal or plastic. The metal plate 402 may be sized smaller, similar or larger than the main body Referring to FIGS. 10-11, the magnetic therapeutic device 100 comprises two permanent magnet elements 204 and 206, with each one designed to be positioned in a substantially aligned position across a person's body part. In one embodiment, this is accomplished by the permanent placement of the magnet elements 204, 206 across the user's or wearer's head as illustrated. Notice that in one embodiment, the magnetic elements are oriented in such a way that one of them has a polarity directed south to north 204, while the other has its polarity oriented in the opposite way, north to south 206. Through this arrangement, the magnetic flux 302 emitted by the magnets is directed across the head or muscle space from one element 204 to the other 206.

Figure 10:
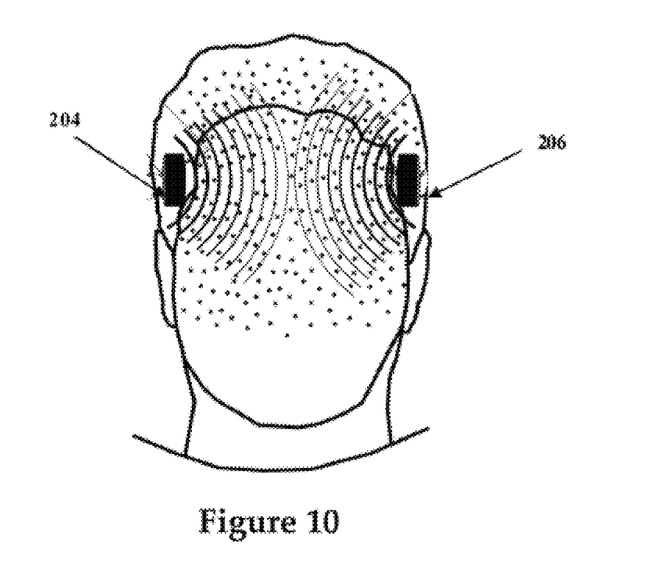
FIGS. 10-11 illustrate the effect of the magnets on the head, according to an exemplary embodiment of the invention.
Figure 11:
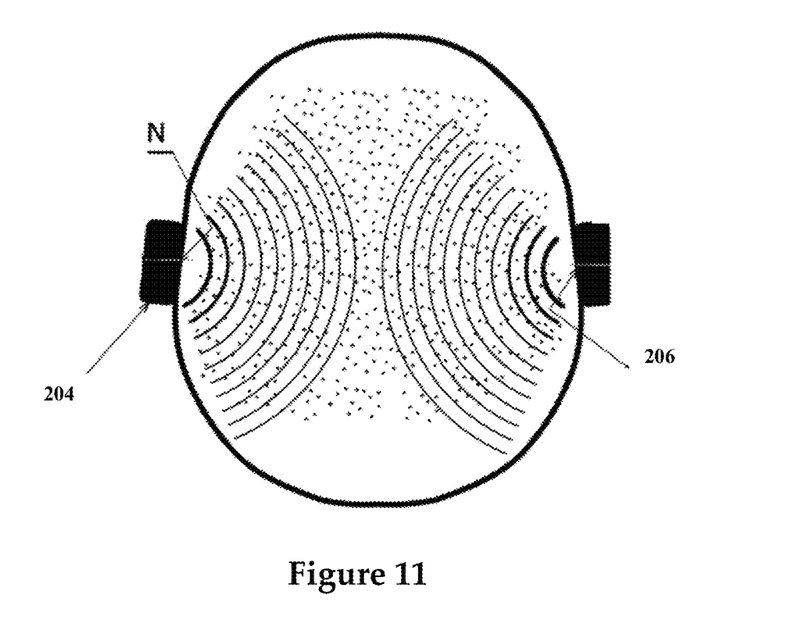
Figure 12:
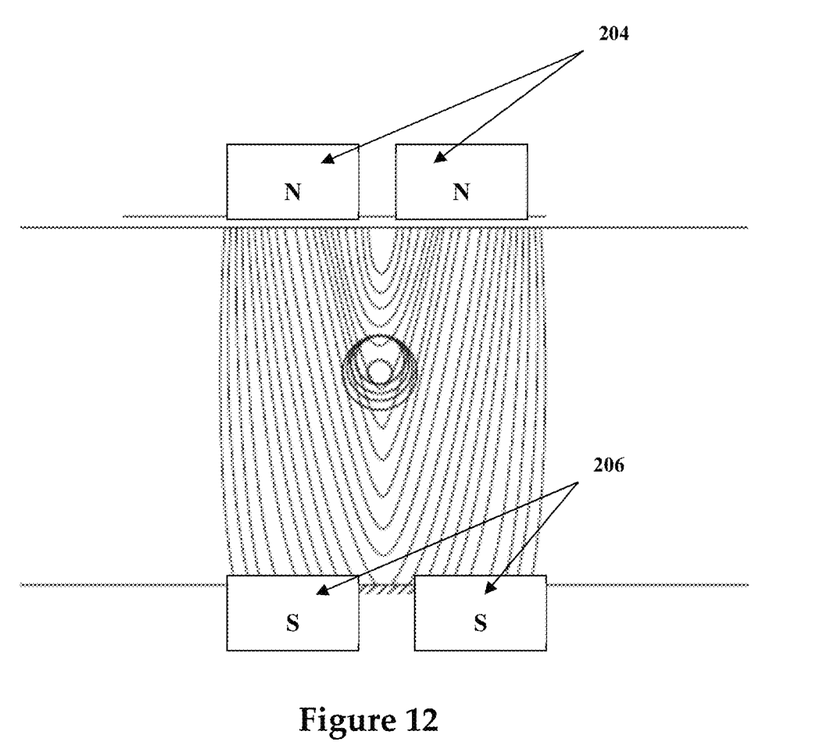
FIG. 12 illustrates a product configuration where N-N and S-S across a body part having a blood vessel, according to an exemplary embodiment of the invention.

In one embodiment, regardless of the relative position—left or right—in the wearer's head, the magnetic elements 204 and 206 should be oriented with an opposite polarity relative to each other. In other words, one of the magnetic element's polarity should be oriented south to north while it's counterpart across the body part being treated should be oriented north to south irrespectively of the head side—left or right—wherein anyone of the particular magnetic elements is located.

In addition to the embodiments shown above, the magnetic elements may be permanently placed in caps, hats, headsets, construction helmets and others. They may be also incorporated in belts, wherein the magnetic elements are mounted and may be tightened up to the convenience of the wearer in such way that the proper fixing and tightness required is achieved. In an alternate embodiment, said magnetic elements may be inserted in lateral pockets of a hat.

A method of use, may be for the magnet assembly (300, 400, 500, 600, 700, 800, 900), to be placed at or near the surface of the body part being treated, with an optional metal plate 902 placed on the other side of the body part or portion. Similarly, the metal plate may be equal or larger in area than the magnet assembly, so any movement will be minimized missing its effect. Alternatively, a similar magnet assembly may be placed on the other side of the body part, with the N-S polarity reversed or matched, so as to increase the effect of the flux.

Alternatively, the unit may be used by moving said magnet assembly (manually and/or mechanically and/or automatically) at different ranges and speeds both horizontally (along or across) as well as vertically (to change the distance to the body part surface) along the area in question. In one embodiment, the size of the metal plate 902 placed opposite is similar to that of the intended movement. Said plate 902 may be held against the body through gravity (laying on a surface), though a belt/vest or other arrangement (which may also hold the magnets in a fixed position).

The above therapies would cause the magnetic flux to affect the blood cells, resulting in potential help to re-establish the natural function of the pancreas, kidneys, liver and other organs. In addition, the magnetic field will have an effect on normal and cancerous cells, as well as in helping with the effects of Alzheimer, multiple sclerosis and other conditions affected by blood circulation and oxygenation. Placing the units over wounds, creates similar advantages through their effect on the blood stream.

Body Therapy

While the above is useful in many organ therapies, they may be seen much more clearly when we see their application to renal and other kidney therapies. In one embodiment, a device is configured to have two or more powerful permanent magnets 204/206. The magnetic fields of these rare earth metal magnets may be mounted in a metallic (both ferrous and/or non-ferrous metals), plastics (including thermoplastics), leather, ceramic, wood or combination thereof, in one exemplary embodiment being 15 cm (6 in.) long by 7.5 cm (3 in.) wide.

In an alternate embodiment, the device may be comprised of a flat pad made of metal, plastic, wood or other suitable material combination (and perhaps covered in real or synthetic leather, with two or more rivets which hold one or more straps, so that the patient or care provider may place their hand within said straps when moving the magnet side against their skin.

When the magnetic fields are placed along any part of the body (not just over the kidneys), the blood flow is increased (as mentioned, in part because of the hemoglobin iron content). The bipolar cells are 'flipped' 212/214 as they go through the N-Pol and S-pol magnets located above the patient's skin. During that movement or rotation, the blood cells (as well as any other having high iron content and bipolar structures) are oxygenated, creating a metabolic reaction which then increases collagen and energizes nearby enzymes, reducing the free radicals that cause the decay of our organisms.

The aforementioned energy release is produced by the increase in the Adenosine triphosphate (ATP) molecule, this is a nucleoside triphosphate, a small molecule used in cells as a coenzyme. It is often referred to as the "molecular unit of currency" of intracellular energy transfer. The increase in synthesis of the ATP molecule drains the metabolic toxins, such as lactic acid, which reduces the "cellular swelling".

This magnetic therapy, using the devices shown above thought the specification, reestablishes tissue and may increase the healing of scars from injuries, as well as bone fractures. It may help in reducing pains along muscles and joints, as it increases the oxygenation along the zone impacted by the magnetic therapy.

The sizes and shapes of these devices may be adjusted, as well as tailored to the patient's needs and idiosyncrasies. The power of the permanent magnets used, as well as their size may also be adjusted depending on the device and the organ/body portion for which therapy is desired. The protocol for magnetic therapies may be implemented and tailored for multiple conditions, such as skin cancer, deep tumors, pain in joints, neurological maladies, stomach and other ulcers, bacteriological sickness, hemorrhoid, acid reflux, stomach ailments, hair loss, renal and pancreatic ailments and others. Creatinine reductions have been observed in patients having renal diseases after using this magnetic therapy.

The aforementioned oxygenation method may be applied to any body part to combat the aforementioned (and other) ailments if we accelerate the movement of the magnets 204/206 magnetic fields over the treated area. This may be accomplished mechanically (via electric, wind up or other motion mechanisms) or manually, so that the bipolar cells get the required rotation acceleration, a faster movement will generate relief and improved conditions on the area treated, as well as anywhere improved cell oxygenation reaches within the bloodstream.

These devices may be mfrd in various sizes and shapes. They may vary in their magnetic field strength, as well as in the number of magnets used in each device, and said magnets may be comprised of ceramic, rare earth and/or other materials.

Referring to FIGS. 13-16 we see 1300/1400 an embodiment 1302 for the treatment of blood as it goes through the blood vessels 1802 near the neck area, which takes advantage of the carotid artery structure at that body portion. Note similar benefits may be accrued from any other cylindrical part of the body (such as legs, arms, waist) where blood flow can be 'sandwiched' within a cross section and subject to the magnetic field crossing.

In one embodiment 1300/1400, one or more pair of N/S polarity magnets (204/206) are placed/held against the body by a belt, strap, choke or similar flexible or semi-flexible neck surrounding member 1302 forcing the blood flow within a vein to be exposed to a magnetic gradient between the magnets 204/206. The magnets 204/206 may be any suitable permanent magnets, but a recommended embodiment may be the use of magnets in the 300 to 20,000 Gauss (or stronger).

The two or more permanent magnet mounting locations are attached along a length of flexible or semi-flexible mechanical linkage component (such as a belt, strap, chain, flexible metal collar), with at least one said mounting locations containing a North Polarity magnet, and at least one other having a South Polarity magnet wherein said mechanical linkage component is adjustable so that it may hold two or more of said magnet locations against a human body part within the circumference formed by said mechanical linkage when closed.

One preferred treatment for the COVID 19 virus has been the application of the device 1302 as a throat choker or neck spanner, for a period of time (say from multiple 15 to 20 minutes sessions, to least two hours a day), so that a significant percentage of the body's blood gets exposed to the magnetic field as it crosses while traveling in the carotid arteries and interconnected blood vessels.

CONCLUSION

In concluding the detailed description, it should be noted that it would be obvious to those skilled in the art that many variations and modifications can be made to the preferred embodiment without substantially departing from the principles of the present invention. Also, such variations and modifications are intended to be included herein within the scope of the present invention as set forth in the appended claims. Further, in the claims hereafter, the structures, materials, acts and equivalents of all means or step-plus function elements are intended to include any structure, materials or acts for performing their cited functions.

It should be emphasized that the above-described embodiments of the present invention, particularly any "preferred embodiments" are merely possible examples of the implementations, merely set forth for a clear understanding of the principles of the invention. Any variations and modifications may be made to the above-described embodiments of the invention without departing substantially from the spirit of the principles of the invention. All such modifications and variations are intended to be included herein within the scope of the disclosure and present invention and protected by the following claims.

The present invention has been described in sufficient detail with a certain degree of particularity. The utilities thereof are appreciated by those skilled in the art. It is understood to those skilled in the art that the present disclosure of embodiments has been made by way of examples only and that numerous changes in the arrangement and combination of parts may be resorted without departing from the spirit and scope of the invention as claimed. Accordingly, the scope of the present invention is defined by the appended claims rather than the forgoing description of embodiments.

I claim:

1. A method for magnetic magnet blood cell oxygenation therapy comprising the steps of:

positioning at or near a human body portion's skin surface a magnetic apparatus, wherein said magnetic apparatus has a handle connected to a main body comprised of two or more permanent magnet mounting locations separated by a spatial gap, wherein said magnetic apparatus main body is made of a durable material capable of keeping each said permanent magnet mounting location aligned to each other, wherein one or more first permanent magnet magnetic elements, each positioned on an individual first permanent magnet magnetic element mounting station with a magnetic polarity North to South, wherein each said first magnetic element is permanently mechanically mounted so that its South polarity side is fixed in place and parallel to said magnetic apparatus main body and one or more second permanent magnet magnetic elements, each positioned on an individual second permanent magnet magnetic element mounting station with a magnetic polarity South to North, wherein each said second magnetic element is permanently mechanically mounted so that its North polarity side is fixed in place and parallel to said magnetic apparatus main body;

wherein at least one of said first permanent magnet magnetic element(s) and at least one of said second permanent magnetic element(s) come in contact with said human body portion's skin;

placing said magnetic apparatus along a portion of a human body; and displacing said magnetic apparatus in a linear fashion along parallel to said human body portion's surface.

2. The method of claim 1 wherein;

said magnetic apparatus linear fashion displacement is accomplished through manual means.

3. The method of claim 1 further comprising;

placing a metal plate having an area size equal or larger to that of the human body portion to be treated so that said human body part rests on said metal plate.

4. The method of claim 3 further comprising;

placing said magnetic apparatus along a portion of a human body; and;

displacing said magnetic apparatus in a linear fashion parallel to said human body portion's surface for a distance that overlaps the area of said metal plate.

5. The method of claim 1 further comprising;

placing another magnetic apparatus on an antipodal side of the human body portion being treated, so that said body portion is sandwiched between said magnetic apparatuses.

6. The method of claim 1 further comprising;

placing another magnetic apparatus on an antipodal side of the human body portion's surface being treated, so that said body portion is sandwiched between said magnetic apparatuses, wherein the magnets are facing each other across the body part in a complementary magnetic polarity configuration.

* * * * *